(12) United States Patent
Amiot

(10) Patent No.: US 6,506,732 B1
(45) Date of Patent: Jan. 14, 2003

(54) ENZYMATIC HYDROLYSATE OF MILK PROTEINS

(75) Inventor: Jean Amiot, Quebec (CA)

(73) Assignee: Universite Laval, Quebec (CA)

(*) Notice: Subject to any disclaimer, the term of this patent is extended or adjusted under 35 U.S.C. 154(b) by 0 days.

(21) Appl. No.: 09/492,766

(22) Filed: Jan. 27, 2000

Related U.S. Application Data

(60) Provisional application No. 60/117,661, filed on Jan. 28, 1999.

(51) Int. Cl.$^7$ ................................................ A61K 38/08
(52) U.S. Cl. ................................ 514/17; 514/2; 514/15; 514/16; 514/18; 514/19; 530/360; 530/361
(58) Field of Search ................................ 514/15–19, 2; 530/360, 361

(56) References Cited

U.S. PATENT DOCUMENTS

| | | | | |
|---|---|---|---|---|
| 4,716,151 A | * | 12/1987 | Jolles | 514/18 |
| 5,021,338 A | * | 6/1991 | Gianna | 435/68.1 |
| 5,166,132 A | | 11/1992 | Gordon | 514/2 |
| 5,314,873 A | | 5/1994 | Tomita et al. | 514/21 |
| 5,486,461 A | * | 1/1996 | Nielsen | 435/68.1 |
| 6,077,558 A | * | 6/2000 | Euber | 426/601 |

FOREIGN PATENT DOCUMENTS

| | | | |
|---|---|---|---|
| GB | 2046591 A | 11/1980 | A61K/7/48 |

OTHER PUBLICATIONS

Jolles Biochim Biophys Acta 365, 335–43 1974.*
Brignon FEBS Lett. 76 274–9, 1977.*
Brignon FEBS Lett. 188, 48–54, 1985.*
Yaguchi Journal of Dairy Science 54, 1725–43, 1971.*
Rose, Journal of Dairy Science 53, 1–17, 1970.*
Roit Immunology, 5th Edition, Mosby International, pp. 301–317 and 341–352; published 1998.*

* cited by examiner

*Primary Examiner*—Christopher S. F. Low
*Assistant Examiner*—David Lukton
(74) *Attorney, Agent, or Firm*—Crowell & Moring LLP

(57) ABSTRACT

The present invention relates to a mixture of soluble hydrophobic peptides of an enzymatic hydrolysate of milk having skin hydrating properties and percutaneous absorption levels of 4 to 5%. The mixture also exhibits wound healing properties but does not have the allergenicity of the milk-protein. One fraction of the mixture is capable of increasing in vitro the growth rate of cell-cultured keratinocytes by at least 50%. The soluble peptides of the fraction have a molecular weight of about 900 daltons ranging from 200 to 1400 daltons, and an average hydrophobicity of 11 Kcal/mole. The soluble peptides are constituted of 66% hydrophobic amino acids and 17% aromatic amino acids, and have aromatic amino acids and other hydrophobic amino acids located at the C- and N-terminal ending in proportion over 85%. Another fraction is capable of increasing the growth rate of cell-cultured fibroblasts by 37% and the production of collagen by 73%. The soluble hydrophobic peptides of the fraction have a molecular weight of about 2000 daltons ranging from 1400 to 2600 daltons. The hydrolysate and peptides of the present invention can be formulated in cosmetic composition, in skin cell culture medium and in wound healing composition.

8 Claims, No Drawings

ENZYMATIC HYDROLYSATE OF MILK PROTEINS

CROSS REFERENCE TO RELATED APPLICATION

This application claims the benefit of U.S. Provisional Application No. 60/117,661, filed Jan. 28, 1999.

BACKGROUND OF THE INVENTION (a) Field of the Invention

The present invention relates to an hydrolysate of milk proteins containing a mixture of hydrophobic and hypoallergenic peptides having molecular weights and hydrophobicity suitable for effective penetration through proteino-lipidic layers of skin, in order to join and to feed the cells of the basal membrane of the epidermis and fibroblasts cells of the dermis.

(b) Description of Prior Art

British Patent application No. 2,046,591 discloses the utilization of whey protein hydrolysate as the active ingredient in skin care composition. The hydrolysate of whey proteins from milk is obtained by the action of an endopeptidase and it consists essentially of peptides having molecular weight in the range from 200 to 5000 daltons. This composition is only suitable for the hydration of skin. It is also known to use casein hydrolysate as hair and skin treating agent. The hydrolysate of casein proteins from milk is obtained by the action of an endopeptidase and a bacterial protease, and it consists of peptides having molecular weight in the range from 300 to 3000 daltons. This agent is suitable in skin care composition for moisturizing property and protective property.

In the prior art referred above, the effectiveness of the peptides to penetrate skin and to promote cell growth, regeneration and repair has not been proven.

U.S. Pat. No. 5,314,873 reveals the utilization of milk proteins hydrolysates, including casein hydrolysate and fraction obtained from such hydrolysate, in cosmetic compositions to activate growth of human cutaneous cells. Hydrolysates are said to contain peptides lower than 1000 daltons and fraction is said to contain aromatic amino acids in an amount of less than 5% by weight of total amino acids and to have proliferation activating property on human cutaneous cells but does not have the antigenicity of the milk protein. Casein was hydrolyzed with a microbial enzyme from Aspergilus and a mixture of pancreatic enzymes to a decomposition level of 41%. Growth of human skin cells, cultured in KGM and KGM modified culture media containing 2% of bovine fetal serum and 100$\mu$g/ml of hydrolysate or fraction of hydrolysate, was used to measure proliferation activity. Proliferation activity of hydrolysate and fractions of hydrolysates was found to be 7 and 13% respectively for keratinocytes, and 4 and 31% respectively for fibroblasts. Antigenicity was determined by ELISA inhibition test using rabbit antiserum and goat anti-rabbit antibody. In the prior art referred above, the effectiveness of peptides to penetrate skin and to promote cells growth has not be proven, as well as the allergenicity in humans and wound healing.

U.S. Pat. No. 5,166,132 reveals that a composition containing casein hydrolysate, carrageenan, poly-vinyl pyrrolidone, methyl paraben or propyl paraben, has wound healing property.

Normal undamaged skin is composed of several layers. The outer layer, usually called the epidermis, is composed of several types of epithelial cells, nerve fibrils, but does not contain blood vessels. Cells that are at or near the base of the epidermis, near the dermo-epidermial junction, are called basal cells. The basal cells generate new keratinocytes that progressively differentiate while migrating to the surface of the skin. During that process, cells produce keratin, a highly resistant fibrous protein that form a solid and water-repellent matrix by interaction with the other structural proteins and lipids of the cells. Below the epidermis is a layer of cells and connective tissue called the dermis. This layer comprises lymph and blood vessels that feed the cells of the epidermis and dermis. Also, hair follicles, sebaceous glands and sweat glands extend from the dermis to the surface of the skin. Fibroblasts cells in the dermis produce collagen, a fibrous protein that forms a structural matrix which increases the strength of the tissue. The proliferation of fibroblasts and the production of collagen are very important during the wound-healing process.

In vitro cell culture from a patient own skin is now used to produce new skin layers or autografts for the treatment of severely burned patients and those suffering important skin loss. Culture media used must contain appropriate nutrients and growth factors such as Epidermal Growth Factor (EGF) to provide rapid growth of undifferentiated keratinocytes cells. Fetal calf serum (FCS), commonly used for that purpose as a source of protein nutrients and growth factors in undifferentiated culture media, is however very expensive. Fetal calf serum is also used in fibroblast culture media to promote cells growth.

It would be highly desirable to be provided with less expensive peptides from casein hydrolysates to replace FCS in undifferentiated culture media.

It would also be highly desirable to be provided with a milk protein hydrolysate or a fraction thereof which may be used in skin cell culture media, or in cosmetic or pharmaceutical formulations.

It would also be highly desirable to be provided. with a milk protein hydrolysate or a fraction thereof which may be used in cosmetic formulations to promote hypoallergenic, skin hydrating and skin regenerating properties.

It would also be highly desirable to be provided with a fraction of milk protein hydrolysate which may be used in skin cell culture media to promote proliferation of cells.

It would also be highly desirable to be provided with a fraction of milk protein hydrolysate which may be used in pharmaceutical preparations to promote percutaneous absorption and wound healing properties.

It would also be highly desirable to be provided with a method for producing a milk protein hydrolysate or a fraction thereof.

SUMMARY OF THE INVENTION

One aim of the present invention is to provide a milk protein hydrolysate or a fraction thereof for use in skin cell culture media, or in cosmetic or pharmaceutical formulations.

Another aim of the present invention is to provide a milk protein hydrolysate or a fraction thereof which may be used in cosmetic formulations to promote hypoallergenic, skin hydrating and skin regenerating properties.

Another aim of the present invention is to provide a fraction of milk protein hydrolysate which may be used in skin cell culture media to promote proliferation of cells.

Another aim of the present invention is to provide a fraction of milk protein hydrolysate which may be used in pharmaceutical preparations to promote percutaneous absorption and wound healing properties.

Another aim of the present invention is to provide a method for producing a milk protein hydrolysate or a fraction thereof to attain the objects and advantages of the present invention.

In accordance with the present invention there is provided a milk protein hydrolysate comprising a first fraction containing a mixture of peptides having a molecular weight of about 900 daltons, ranging from 200 to 1400 daltons, and a hydrophobicity of about 11 Kcal/mole, and a second fraction containing a mixture of soluble hydrophobic peptides having a molecular weight of about 2000 daltons, ranging from 1400 to 2600 daltons. The mixture of peptides having a molecular weight of about 900 daltons contains a total hydrophobic amino acids concentration and an aromatic amino acids concentration of at least 65% and 17% respectively; the peptides have aromatic amino acids and other hydrophobic amino acids located at the C- and N-terminal ending in proportion over 85%.

Still in accordance with the present invention, there is provided an enzymatic hydrolysate of milk proteins comprising a mixture of soluble peptides comprising a first fraction containing peptides of a molecular weight ranging from 200 daltons to 1400 daltons and having average hydrophobicity of 11 Kcal/mole, a second fraction containing hydrophobic peptides of molecular weight ranging from 1400 to 2600 daltons. The hydrolysate has low allergenicity and skin hydration property. Preferred peptides of the present invention are, without limitation, selected from the group consisting of ALPQYL (SEQ ID NO:1), SPA-QILQWQVL (SEQ ID NO:2), LLY, YL, QGPIVLNPW (SEQ ID NO:3),VLVL (SEQ ID NO:4), LYQGPIVL (SEQ ID NO:5), VPLGTQY (SEQ ID NO:6), LQSW (SEQ ID NO:7), VLPVPQK (SEQ ID NO:8), IPIQY (SEQ ID NO:9), YVPLGTQY (SEQ ID NO:10), YGLNYYQQKPVA (SEQ ID NO:11), LYQEPVL (SEQ ID NO:12), and INNQ-FLPYPY (SEQ ID NO:13).

In accordance with a preferred embodiment of the present invention, there is provided a fraction of an hydrolysate of milk proteins comprising a mixture of peptides having a molecular weight ranging from 200 daltons to 1400 daltons and a hydrophobicity of about 11 Kcal/mole. The peptides are constituted of at least 66% hydrophobic amino acids and 17% aromatic amino acids, and have aromatic amino acids and other hydrophobic amino acids located at the C- and -N-terminal endings in proportion over 85%. The peptides have low allergenicity and a percutaneous absorption of about 5%, and are capable of increasing the growth rate of human keratinocytes in vitro culture by at least 50%.

In accordance with another preferred embodiment of the present invention, there is provided a fraction of an hydrolysate of milk proteins comprising a mixture of hydrophobic peptides having a molecular weight ranging from 1400 to 2600 daltons. The peptides have low allergenicity and a percutaneous absorption of about 4%, and are capable of increasing the growth rate of human fibroblasts in vitro culture by at least 35% and the production of collagen by at least 70%.

Still in accordance with the present invention, there is provided an hypoallergenic and moisturizing cosmetic composition comprising the hydrolysate as described above in a proportion from 1% to 5% by weight in association with a cosmetically suitable skin compatible topical carrier.

In accordance with the present invention, there is provided an hypoallergenic and skin regenerating cosmetic composition comprising the fraction of an hydrolysate of milk proteins comprising a mixture of peptides having a molecular weight ranging from 200 daltons to 1400 daltons and a hydrophobicity of about 11 Kcal/mole, in a proportion from 1% to 5% by weight in association with a cosmetically suitable skin compatible topical carrier.

In accordance with the present invention, there is also provided a keratinocytes culture medium comprising the fraction of an hydrolysate of milk proteins comprising a mixture of peptides having a molecular weight ranging from 200 daltons to 1400 daltons and a hydrophobicity of about 11 Kcal/mole, in a proportion of from 0.002% to 0.05% by volume in association with an acceptable carrier.

In accordance with the present invention, there is also provided a fibroblasts culture medium comprising the fraction of an hydrolysate of milk proteins comprising a mixture of hydrophobic peptides having a molecular weight ranging from 1400 to 2600 daltons, in a proportion of from 0.002% to 0.05% by volume in association with an acceptable carrier.

In accordance with the present invention, there is also provided an hypoallergenic wound healing composition comprising the hydrolysate as described above, in a proportion from 1% to 5% by weight in association with a suitable skin compatible topical carrier.

In accordance with the present invention, there is also provided a method for producing an enzymatic hydrolysate as defined above, comprising the step of contacting milk proteins with at least one enzyme selected from the group consisting of pepsin and chymotrypsin under suitable condition and for a time sufficient to obtain a degree of hydrolysis of 1.0 to 10% of the milk proteins.

The mixtures of peptides of the present invention can be used in moisturizing and regenerating cosmetic compositions, in culture media for in vitro production of human skin cells and in pharmaceutical compositions for wound healing.

DETAILED DESCRIPTION OF THE INVENTION

In accordance with the present invention, it was found that the allergenicity of milk proteins is most effectively reduced by hydrolysis with pepsin or chymotrypsin, compared to other enzymes or combinations of enzymes. Hydrolysis of casein with the same two enzymes is also shown to produce bioactive hydrophobic peptides. Further separation of peptides from such an hydrolysate by size exclusion, ion-exchange and/or hydrophobic interaction chromatographies give one fraction containing soluble peptides containing total hydrophobic amino acids and aromatic amino acids in concentrations higher than 66% and 15% respectively and specially located at the C-terminal ending of the peptides. Percutaneous absorption of peptides from the fraction is shown to be 5% and over 50% increase in growth of human keratinocytes is obtained with cells cultured in a well defined culture medium containing as low as 20 $\mu$g/ml fraction but no fetal calf serum. Another fraction of the milk protein hydrolysate is shown to contain soluble hydrophobic peptides having a M.W. of about 2000 daltons. Percutaneous absorption of peptides from the fraction is shown to be 4%. Over 35% increase in growth of human fibroblasts and over 70% increase in production of collagen are obtained with cells in a culture medium containing 200 $\mu$g/ml fraction. The present invention is based on these findings.

The present invention thus relates to an enzymatic hydrolysate of milk protein produced under specific enzymatic conditions in order to contain a mixture of soluble peptides, one fraction of which having a molecular weight of about 900 daltons and a hydrophobicity of about 11 Kcal/mole and another fraction containing hydrophobic peptides having a molecular weight of about 2000 daltons, which have reduced allergenicity, and which can be used in cosmetic emulsions, lotions and gels to promote hydrating and skin regenerating properties of such formula.

Topical compositions for hydrating dry skin give good results when a) the ingredients, such as fats and proteins, act on the skin surface as occlusive agent to restrain water loss by evaporation, and b) when hydroscopic agents, such as amino acids and peptides, contribute to fix water in the upper layers of the epidermis. However, in order to penetrate more deeply into skin to join and feed the basal cells and fibroblasts, peptides and amino acids must have low molecular weight as well as chemical structure allowing miscibility with hydrophobic lipids and more or less soluble proteins of skin. Nutrients required for normal growth and for regeneration of cutaneous cells, as well as for skin repair during wound healing process, include eight essential amino acids, six of which being hydrophobic amino acids including three aromatic amino acids. Only a few protein sources, including milk proteins, are known to contain high levels of essential amino acids.

Hence, in accordance with another aspect of the present invention, fractions of milk protein hydrolysate, produced by using specific separation means and conditions, consisting of mixtures of soluble peptides having percutaneous absorption properties and growth promoting property on skin cells (keratinocytes and fibroblasts) and wound healing properties can be used in skin cell culture media or in wound healing pharmaceutical formulations. Peptides of one fraction have a molecular weight of about 900 daltons ranging from 200 to 1400 daltons and a hydrophobicity of about 11 Kcal/mole, and contain a concentration of total hydrophobic amino acids and aromatic amino acids of at least 65% and 17% respectively, and have aromatic amino acids and other hydrophobic amino acids located at the C- and N-terminal ending in proportion over 85%. Hydrophobic peptides of another fraction have a M.W. of about 2000 daltons, ranging from 1400 to 2600 daltons.

Any milk protein sold in the market such as casein or its fractions, and whey protein or its fractions, and milk protein or whey protein concentrates, can be used to produce the hydrolysate of the present invention. Preferably, milk protein concentrate or casein is used.

The enzymes used for the hydrolysis are limited to endopeptidases with specific affinity and activity for aromatic and other hydrophobic amino acids located in the polypeptide chains of the protein, such as pepsin, chymotrypsin or neutrase. Preferably, pepsin and/or chymotrypsin is used to produce the hydrolysate of the present invention.

Hydrolysis is carried out at a temperature of about 35° C. to about 42° C. The pH of the solution is adjusted close to the optimum pH value of the enzyme throughout the reaction, preferably 2.0 for pepsin and 8.0 for chymotrypsin. Protein concentration is between 1%–10%, preferably 5%, and enzyme-to-protein ratio is between 1/25 to 1/1000, preferably 1/100 depending on the length and the extent of hydrolysis required, which is between 1%–10% degree of hydrolysis. The preferred degree of hydrolysis (D.H.), percentage of links between amino acids in the protein that are broken, is 6% for reaction with pepsin and between 6%–10% for chymotrypsin. The enzymatic reaction may be stopped for example by raising the pH to 8.0 for pepsin, by heat inactivation at 80° C. for 3 minutes for pepsin and chymotrypsin, by using ultrafiltration to remove the enzymes, or by filtration for processes with immobilized enzymes.

The hydrolysate of the present invention can be lyophilized and readily used in cosmetic formulations. The hydrolysate can also be fractionated by using ultrafiltration, size exclusion chromatography, ion exchange chromatography, and/or hydrophobic interaction chromatography. Fractions obtained can be desalted by dialysis, chromatography, membrane processing or electrodialysis.

The fractions of hydrolysate obtained, one fraction containing peptides having a molecular weight of about 900 daltons, ranging from 200 to 1400 daltons, and a hydrophobicity of about 11 Kcal/mole, and another fraction containing hydrophobic peptides having a M.W. of about 2000 daltons ranging from 1400 to 2600 daltons, can be used in skin cells culture media and in topical formulations for cosmetic and pharmaceutical applications.

The preferred hydrolysate used for a topical cosmetic composition, such as a cream, is the lyophilized milk protein hydrolysate. This hypoallergenic hydrolysate contains hydrophobic peptides with a low molecular weight, ranging from 200 to 1400 daltons (200 Da<M.W.<1400 Da), and hydrophobic peptides with a high molecular weight, ranging from 1400 to 2600 daltons (1400 Da<M.W<2600 Da), which are suitable for emulsions, lotions or gels. Although some soluble and hydrophobic peptides have a percutaneous absorption and skin regenerating properties, some other hydrophobic peptides contribute to hydratation property as occlusive agents in topical compositions.

Since the hydrolysate contains the active ingredients, the composition intended for cosmetic topical use normally contains a carrier compatible with the method of administration selected. For example, for preparing creams and similar products, a paste-like, semi-fluid or fluid ointment base is used which, of course, is non-toxic to the body and which is capable of being emulsified with the hydrolysate (oil-in-water and water-in-oil emulsion) . Examples of ingredients for the base include cetyl alcohol, lanolin, petroleum jelly, liquid paraffin and polyoxyethylene sorbitan esters such as the palmitates, oleates and stearates, and these substances may all be used either separately or in combination for preparing the base. This base preferably also contains triglycerides, containing essential fatty acids and, optionally, a high proportion of liposoluble vitamins, long-chain fatty alcohols, esters of branched-chain fatty acids and emulsive monoglycerides. Formulations intended for application to base skin desirably have a chemical composition as close as possible to that of human sebum. In certain cases, one or more emulsifiers and/or surfactants may be incorporated in the composition, depending on the type of formulation required.

The composition according to the invention may also be presented in the form of aqueous dispersions (lotions such as, for example, pre-shave or after-shave lotions), liquid emulsions (body milks, cleansing milks), viscous emulsions (masks), aqueous or anhydrous gels. The composition according to the invention may also be incorporated in make-up foundations and hair care products.

The composition according to the invention may be used as a topical cosmetic, for example in the form of a cream or a milk.

The preferred fraction of the hydrolysate used in a culture medium for in vitro growth of keratinocytes is the fraction of the milk protein hydrolysate which contains the low molecular weight peptides of 200 to 1400 daltons having hydrophobicity of about 11 Kcal/mole and constituted of at least 65% of hydrophobic amino acids and 17% of aromatic amino acids and having aromatic amino acids and other hydrophobic amino acids located at the C- and N-terminal ending in proportion over 85%. The preferred fraction of the hydrolysate used in a culture medium for in vitro growth of fibroblasts is the fraction of the milk protein hydrolysate which contains the hydrophobic peptides of high molecular weight of 1400 to 2600 daltons.

Since the fractions of the hydrolysate of the present invention which contain the mixture of low molecular weight and highly hydrophobic peptides are the active ingredients for in vitro culture of skin cells, they may be incorporated into appropriate culture media which act as pharmaceutically acceptable carriers. For example, the culture media which may serve as a carrier are MCDB 153®, MEM, DMEM, MCDB 151® and HAM-F12® (sold by Sigma Chemical Company, St-Louis, Mo.), SFM® (sold by Gibco) and KBM® (sold by Clonetics Corporation, San Diego, Calif.).

The present invention will be more readily understood by referring to the following examples which are given to illustrate the invention rather than to limit its scope.

EXAMPLE 1

Moisturizing and Regenerating Cosmetic Cream Containing Hydrolysate from Milk Protein Concentrate Preparation of the Milk Protein Hydrolysate Low heat skim milk powder (S.M.) is reconstituted at approximately 33% protein on dry basis (D.B.) and about 10% total solids with distilled water. A three fold concentrate is obtained by ultrafiltration (UF) using UF membranes with 50,000 M.W. cut-off which results in a product having approximately 55% protein on D.B. Diafiltration is then performed on the concentrate with distilled water, preferably five times, resulting in a milk protein concentrate (M.P.C.) having a content in protein and lactose of about 84% and 0.16% respectively on D.B.

The pH of the solution is adjusted to 8.1 and the temperature is brought at 37° C. The enzymatic hydrolysis is conducted with chymotrypsin. The enzyme substrate ratio is 1/250. The enzymatic reaction is stopped by heat inactivation, 80° C. for 3 minutes, after reaction time of approximately 13, 37 or 96 minutes to obtain hydrolysate with 1.5%, 3.0% or 6.0% degree of hydrolysis (D.H.) respectively.

The hydrolysates of the present invention contain as active principles, hydrophobic peptides of average molecular weight of 900 daltons, and hydrophobic peptides of average molecular weight of 2000 daltons. The 6% D.H. milk protein hydrolysate with chymotrypsin is preferred for its higher content of active peptides (moisturizing and skin regenerating property) and functional properties (solubility, emulsion and gel related properties).

Cosmetic Cream

A white cream of oil-in-water emulsion type is prepared by mixing the ingredients listed in Table 1.

TABLE 1

| Part | Ingredients | % |
|---|---|---|
| A. | Glyceryl stearate | 3.65 |
|  | Decyl oleate | 7.30 |
|  | PEG-20 glyceryl stearate | 1.22 |
|  | Ceteareth-12 | 1.22 |
|  | Cethyl alcohol | 0.61 |
| B. | Milk Protein Hydrolysate | 1.00 |
| C. | n-propyl p-hydroxybenzoate | 0.33 |
|  | p-hydroxybenzoic acid methyl ester | 0.66 |
| D. | Glycerol | 3.00 |
|  | Deionized water | balance to |

For better stability of the cream, 10% of a 2% solution of Carbopol 940 and 0.18% of triethanolamine is added.

The procedure comprises heating separately the fat phase (Part A) and the aqueous phase (Part D) at 75° C. Part A is mixed with part D with adequate stirring. Carbopol 940 and triethanolamine can be prepared separately and added after Parts A and D are mixed. The mixture is then cooled down at 40° C. and Part C is added. At 30° C., the hydrolysate (Part B) is added, preferably the 6% D.H. milk protein hydrolysate with chymotrypsin. Agitation is reduced until the mixture is cooled at 28° C.

This cream has a very good moisturizing effect since the occlusive property measured with gelatin cell method is 70.8% compared to 37.0% for cream with no hydrolysate. Furthermore, the hydrolysate has a whitening effect on the cream, and the emulsion is stable for 12 months at 250° C.

EXAMPLE 2

Skin Cells Culture Media Containing Fractions of Milk Protein Hydrolysate

Preparation of the Fractions from Milk Protein Hydrolysate

The 6% D.H. milk protein hydrolysate with chymotrypsin is centrifuged. Soluble fraction is recuperated and filtered on preparative Sephadex™ G-25 size exclusion gel chromatography column using deionized water as the mobile phase. Four fractions are recuperated. The first fraction (F1) contains polypeptides of average molecular weight of 2000 daltons ranging from 1400 to 2600 daltons. The second fraction (F2) contains peptides of intermediate molecular weight between F1 and F3. The third fraction (F3) contains peptides of average molecular weight of 900 daltons ranging from 200 to 1400 daltons. The fourth fraction contains mostly salts and free amino acids.

Further separation of the third fraction (F3) on preparative High Pressure Liquid Chromatography (HPLC) using TSK G2000 SW column and a 5 mM ammonium acetate buffer mobile phase adjusted to pH 6.5 gives five subfractions (SF1 to SF5). Composition of subfraction four (SF4), obtained by RP-HPLC using C-18™ column, containing fifteen peptides having average molecular weight of 900 daltons (200 to 1400 daltons) and average hydrophobicity of 11.7 Kcal/mole (5 to 20 Kcal/mole) is presented in Table 2.

TABLE 2

| Amino Acids Composition | Molecular Weight (daltons) | Hydrophobicity (Kcal/mole) | Location milk proteins |
|---|---|---|---|
| ALPQYL | 704 | 10.9 | Casein α-s2 175–180 |
| SPAQILQWQVL | 1282 | 15.5 | Casein κ 69–79 |
| LLY | 407 | 7.7 | Casein β 191–193 |
| YL | 294 | 5.3 | Casein α-s1 91–92 |

TABLE 2-continued

| Amino Acids Composition | Molecular Weight (daltons) | Hydrophobicity (Kcal/mole) | Location milk proteins |
|---|---|---|---|
| QGPIVLNPW | 1023 | 15.1 | Casein α-s2 101–109 |
| VLVL | 443 | 8.2 | β-Lactoglobulin 92–95 |
| LYQGPIVL | 902 | 17.7 | Casein α-s2 99–106 |
| VPLGTQY | 777 | 9.9 | Casein α-s1 167–173 |
| LQSW | 533 | 5.3 | Casein β 140–143 |
| VLPVPQK | 780 | 12.3 | Casein β 170–176 |
| IPIQY | 633 | 11.3 | Casein κ 26–30 |
| YVPLGTQY | 940 | 12.7 | Casein α-s1 166–173 |
| YGLNYYQQKPVA | 1444 | 14.4 | Casein κ 38–49 |
| LYQEPVL | 861 | 9.3 | Casein β 192–198 |
| INNQFLPYPY | 1268 | 19.9 | Casein κ 51–60 |

Skin Cells Culture Media a) Keratinocyte Culture Medium

Culture medium MCDB 153 (Sigma, St-Louis, Mo.) containing bovine pituitary extract (0.4%), insulin (5 μg/ml), hydrocortisone (0.4 μg/ml), human EGF (10 μg/ml), phosphoethanolamine (0.1 mM), penicillin G (100 iu/ml), gentamicin (25 μg/ml) and with calcium concentration adjusted to 0.15 mM, is supplemented with Fraction F3 and subfraction SF4 of the 6% D.H. milk protein hydrolysate with chymotrypsin at a concentration of 200 μg/ml and 20 μg/ml respectively.

Human keratinocytes cells are fed with the media changed daily and maintained at 37° C. under controlled atmosphere for 11 days. Microscopic exams are made every two days and cells are counted at the end of the experience with a Coulter Counter after trypsinisation.

Compared to the unsupplemented medium, culture medium supplemented with 200 μg/ml of fraction F3 gives a 60% increase in growth of keratinocytes and medium supplemented with 20 μg/ml of subfraction SF4 gives a 52% increase. Also, confluency of epidermial sheet is attained in 8 to 10 days in medium supplemented with F3 and SF4 and in 12 to 14 days with unsupplemented medium. Microscopic exam reveals that the cells cultured in medium supplemented with F3 and SF4 are undifferentiated, smaller and packed, which is required for clinical purposes.

b) Fibroblasts Culture Medium

Culture medium DMEM (Flow Laboratories, Mississauga, Ontario, Canada) containing veal fetal serum (5%), penicillin G (100 iu) and streptomycin (50 μg/ml) is supplemented with fraction F1 from 6% D.H. milk protein hydrolysate with chymotrypsin at a concentration of 200 μg/ml.

Human fibroblasts are fed with the culture medium changed every two days and maintained at 37° C. under controlled atmosphere for 10 days. After trypsinisation, cells are counted with a Coulter Counter and synthesis of protein and collagen are measured.

Compared to the unsupplemented medium, culture medium supplemented with 200 μg/ml of F1 gives a 37% increase in growth of fibroblasts, a 62% increase in synthesis of proteins and 73% increase in production of collagen. The proportion of the different types of collagen is not modified.

EXAMPLE 3

Skin Cells Culture Media Containing Fractions of Casein Hydrolysate

Preparation of the Casein Hydrolysate

Casein (ICN, Cleveland, Ohio) is reconstituted (approximately 89% protein on D.B.) at about 3.5% total solids with distilled water.

For hydrolysis with pepsin, the pH of the solution is adjusted to 2.0 and the temperature is brought at 40° C. Pepsin is added to an enzyme substrate ratio of 1/100 and hydrolysis is conducted for 180 minutes under controlled temperature, pH and agitation. Reaction is stopped by ultrafiltration using membrane with 30,000 daltons cut off.

For hydrolysis with chymotrypsin, the pH of the solution is adjusted to 8.0 and temperature is brought at 40° C. Chymotrypsin is added to an enzyme substrate ratio of 1/100 and hydrolysis is conducted for 180 minutes under controlled temperature, pH and agitation. Reaction is stopped by ultrafiltration using membrane with 30000 daltons cut off.

Characteristics of the hydrolysates, presented in Table 3, indicate that the pepsin and chymotrypsin hydrolysates are constituted of peptides of molecular weight between 200 daltons and 1400 daltons in proportions of 53% to 73% respectively and that the proportions of hydrophobic peptides with polarity lower than 8.3 is 71% and 90% respectively.

TABLE 3

| Characteristics/ Hydrolysates | Pepsin | Chymotrypsin |
|---|---|---|
| Degree of Hydrolysis (D.H.) (%) | 5.7 | 8.9 |
| Peptides (%) with 200 Da < M.W. < 1400 Da | 53 | 73 |
| Hydrophobic peptides (polarity <8.3) (%) | 90 | 71 |

Preparation of the Fractions from the Casein Hydrolysates

The pepsin and chymotrypsin casein hydrolysates are centrifuged and the soluble fractions are recuperated. Preparative anion exchange chromatography on HPLC using a linear gradient of acetonitril (60%) and trifluoroacetic acid (0.1%) is used to obtain four fractions from each hydrolysate, of which only the three first ones are kept.

Fractions are desalted by preparative RP-HPLC with a mobile phase constituted of acetonitril (60%) and trifluoroacetic acid (0.1%).

The characteristics of the fractions, P1, P2 and P3 from the casein hydrolysate with pepsin, and C1, C2, and C3 from the hydrolysate with chymotrypsin, are presented in Table 4. Results indicate that all fractions except P3 are constituted of peptides with M.W. between 200 daltons and 1400 daltons in proportion of at least 50% and that the proportion of hydrophobic peptides with polarity lower than 8.3 is from 44% to 88%, corresponding approximately to their content in aromatic and other hydrophobic amino acids.

TABLE 4

| Characteristics/ Hydrolysates | Fractions | Pepsin | Chymotrypsin |
|---|---|---|---|
| Peptides from the hydrolysate (%) | 1 | 58 | 45 |
| | 2 | 23 | 25 |
| | 3 | 10 | 12 |
| Peptides (%) with 200 Da < M.W. < 1400 Da | 1 | 50 | 59 |
| | 2 | 51 | 53 |
| | 3 | 43 | 53 |
| Hydrophobic peptides (polarity <8.3) (%) | 1 | 88 | 44 |
| | 2 | 53 | 50 |
| | 3 | 68 | 60 |

Keratinocytes Culture Media

Culture medium MCDB 153 (Sigma, St-Louis, Mo.), containing bovine pituitary extract (0.4%), insulin (5 μg/ml), hydrocortisone (0.4 μg/ml),-human EGF (10 μg/ml), phosphoethanolamine (0.1 mM), penicillin G (100 iu/ml), gentamicin (25 μ/ml) and with calcium concentration adjusted to 0.15 mM, is supplemented with fractions of the hydrolysates refereed above at a concentration of 20 μg/ml.

Human keratinocytes cells are fed with the media changed daily and maintained at 37° C. under controlled atmosphere for 11 days. Microscopic examinations are made every two days and cells are counted at the end of the experience with a Coulter Counter after trypsinisation.

Compared to the unsupplemented medium, culture medium supplemented with 20 μg/ml of fractions from casein hydrolysis with pepsin and chymotrypsin gives increase in growth of keratinocytes up to 58% as presented in Table 5.

TABLE 5

| | Fractions | Pepsin | Chymotrypsin |
|---|---|---|---|
| Keratinocytes growth increase (%) | 1 | 58 | 54 |
| | 2 | 41 | 22 |
| | 3 | 38 | 16 |

EXAMPLE 4

Ingredient for Wound Healing Preparations
Preparation of the Ingredient
Fractions F1 and F3 from the 6% D.H. milk protein hydrolysate with chymotrypsin having low allergenicity is prepared as previously described in Examples 1 and 2.
Percutaneous Absorption of the Ingredient Fractions F1 and F3 from the 6% D.H. milk protein hydrolysate with chymotrypsin are treated with $^{125}$Iodine to produce radiolabelled peptides.

Percutaneous absorption of the peptides is measured with Franz diffusion apparatus using nude rats skins on which samples of radiolabelled fractions F1 and F3 are placed. Percutaneous absorption values are obtained by measuring with a y-Counter the proportion of $^{125}$Iodine passing through the skin (epidermal and dermal layers) in 24 hours.

Results indicate a 4 and 5% percutaneous absorption of peptides from fractions F1 and F3 respectively, which indicates that peptides from fraction F3 reach keratinocytes in the epidermal layer of skin, and that peptides from fraction F1 reach fibroblasts in the dermal layer of skin.
Effect of the Ingredient on the Cutaneous Cells As reported previously in Example 2, low molecular weight and highly hydrophobic peptides from fraction F3 of the 6% D.H. milk protein hydrolysate with chymotrypsin produces a 60% increase in growth rate of human keratinocytes (epidermis); fraction F1 from the same hydrolysate produces a 37% increase for fibroblasts (dermis), a 62% increase in synthesis of proteins and a 73% increase in production of collagen by fibroblasts of the dermis.
Wound Healing Property Fraction F3 from the 6% D.H. milk protein hydrolysate combine effective percutaneous absorption (5%) with growth promoting activity on epidermal cells (60%); fraction F1 has growth promoting activity on dermal cells (37%) as well as improvement in synthesis of proteins (62%) and collagen (73%). All those properties including hypoallergenicity of the fractions of the 6% D.H. milk protein hydrolysate are suitable to accelerate the wound healing process. Mixtures of peptides of fractions F1 and F3 can therefore be used as the active agents in pharmaceutical wound healing composition in association with a skin compatible topical carrier.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A crude fraction of a hydrolysate of casein-containing milk proteins comprising a mixture of peptides obtained by hydrolysis of said milk proteins with at least one of pepsin or chymotrypsin to a degree of hydrolysis of 1 to 10%, and subsequent fractionation to obtain a fraction having a molecular weight ranging from 200 daltons to 1400 daltons and a hydrophobicity of about 11 Kcal/mole, said peptides being constituted of at least 66% hydrophobic amino acids and 17% aromatic amino acids, and having aromatic amino acids and other hydrophobic amino acids located at the C- and N-terminal endings in proportion over 85%, said peptides having low allergenicity and a percutaneous absorption of about 5%, wherein said fraction increases the growth rate of human keratinocytes in vitro culture by at least 50%, and wherein said fraction is substantially free from free amino acids.

2. The crude fraction of claim 1, wherein said peptides are selected from the group consisting of ALPQYL (SEQ ID NO: 1), SPAQILQWQVL (SEQ ID NO:2), LLY, YL, QGPIVLNPW (SEQ ID NO:3), VLVL (SEQ ID NO:4), LYQGPIVL (SEQ ID NO:5), VPLGTQY (SEQ ID NO:6), LQSW (SEQ ID NO:7), VLPVPQK (SEQ ID NO:8), IPIQY (SEQ ID NO:9), YVPLGTQY (SEQ ID NO:10), LYQEPVL (SEQ ID NO:12), and INNQFLPYPY (SEQ ID NO:13).

3. A crude fraction according to claim 1, wherein the degree of hydrolysis is 1.5%.

4. A crude fraction according to claim 1, wherein the degree of hydrolysis is 3%.

5. A cosmetic composition comprising the fraction of claim 1 in a proportion of from 1% to 5% by weight in association with a cosmetically suitable skin compatible topical carrier.

6. A composition comprising the crude fraction of claim 1 in a proportion from 1% to 5% by weight in association with a skin compatible topical carrier.

7. A keratinocytes culture medium comprising the fraction of claim 3 in a proportion of from 0.002% to 0.05% by volume in association with an acceptable carrier.

8. A method for producing a crude fraction as defined in claim 1 comprising the steps of contacting casein-containing milk proteins with at least one enzyme selected from the group consisting of pepsin and chymotrypsin under suitable conditions and for a time sufficient to obtain a degree of hydrolysis of 1.0 to 10% of said milk proteins, and isolating a fraction having a molecular weight ranging from 200 Daltons to 1400 Daltons.

* * * * *

SEQUENCE LISTING

<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 1

Ala Leu Pro Gln Tyr Leu
1               5

<210> SEQ ID NO 2
<211> LENGTH: 11
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 2

Ser Pro Ala Gln Ile Leu Gln Trp Gln Val Leu

-continued

```
<210> SEQ ID NO 3
<211> LENGTH: 9
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 3

Gln Gly Pro Ile Val Leu Asn Pro Trp
1               5

<210> SEQ ID NO 4
<211> LENGTH: 4
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 4

Val Leu Val Leu
1

<210> SEQ ID NO 5
<211> LENGTH: 8
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 5

Leu Tyr Gln Gly Pro Ile Val Leu
1               5

<210> SEQ ID NO 6
<211> LENGTH: 7
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 6

Val Pro Leu Gly Thr Gln Tyr
1               5

<210> SEQ ID NO 7
<211> LENGTH: 4
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 7

Leu Gln Ser Trp
1

<210> SEQ ID NO 8
<211> LENGTH: 7
<212> TYPE: PRT
<213> ORGANISM: Artificial Sequence
<220> FEATURE:
<223> OTHER INFORMATION: Peptide from enzymatic hydrolysate of milk
```

```
                               proteins

<400> SEQUENCE: 8

Val Leu Pro Val Pro Gln Lys
 1               5

<210> SEQ ID NO 9
<211> LENGTH: 5
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 9

Ile Pro Ile Gln Tyr
 1               5

<210> SEQ ID NO 10
<211> LENGTH: 8
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 10

Tyr Val Pro Leu Gly Thr Gln Tyr
 1               5

<210> SEQ ID NO 11
<211> LENGTH: 12
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 11

Tyr Gly Leu Asn Tyr Tyr Gln Gln Lys Pro Val Ala
 1               5                  10

<210> SEQ ID NO 12
<211> LENGTH: 7
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 12

Leu Tyr Gln Glu Pro Val Leu
 1               5

<210> SEQ ID NO 13
<211> LENGTH: 10
<212> TYPE: PRT
<213> ORGANISM: Artificial Sequence
<220> FEATURE:
<223> OTHER INFORMATION: Peptide from enzymatic hydrolysate of milk
      proteins

<400> SEQUENCE: 13

Ile Asn Asn Gln Phe Leu Pro Tyr Pro Tyr
 1               5                  10
```